United States Patent
Ishiba et al.

(10) Patent No.: US 7,505,149 B2
(45) Date of Patent: Mar. 17, 2009

(54) APPARATUS FOR SURFACE INSPECTION AND METHOD AND APPARATUS FOR INSPECTING SUBSTRATE

(75) Inventors: Masato Ishiba, Kyoto (JP); Jun Kuriyama, Fukuchiyama (JP); Kiyoshi Murakami, Kyoto (JP); Teruhisa Yotsuya, Kyoto (JP)

(73) Assignee: OMRON Corporation, Kyoto (JP)

( * ) Notice: Subject to any disclaimer, the term of this patent is extended or adjusted under 35 U.S.C. 154(b) by 324 days.

(21) Appl. No.: 11/056,739

(22) Filed: Feb. 11, 2005

(65) Prior Publication Data
US 2005/0190361 A1 Sep. 1, 2005

(30) Foreign Application Priority Data
Feb. 27, 2004 (JP) ............................ P2004-052800
Feb. 9, 2005 (JP) ............................ P2005-032845

(51) Int. Cl.
*G01N 21/88* (2006.01)
(52) U.S. Cl. ................. 356/612; 356/237.1; 356/237.5; 382/150
(58) Field of Classification Search ... 356/237.1–237.6, 356/243.4–243
See application file for complete search history.

(56) References Cited

U.S. PATENT DOCUMENTS

| | | | | |
|---|---|---|---|---|
| 6,023,663 A | * | 2/2000 | Kim | ............................ 702/81 |
| 6,040,895 A | * | 3/2000 | Haas | ............................ 355/70 |
| 2003/0169418 A1 | * | 9/2003 | Fujii et al. | ............... 356/237.2 |

FOREIGN PATENT DOCUMENTS

| | | |
|---|---|---|
| JP | 02-190750 | 7/1990 |
| JP | 03-142303 | 6/1991 |

OTHER PUBLICATIONS

Japan patent application No. 2005-032845, Examination Report dated Jun. 27, 2006.

* cited by examiner

*Primary Examiner*—Roy M Punnoose
*Assistant Examiner*—Tara S Pajoohi
(74) *Attorney, Agent, or Firm*—Weaver Austin Villeneuve & Sampson LLP

(57) ABSTRACT

A target object has its surface condition inspected by having its image taken from above while being irradiated by red, green and blue light beams at different elevation angles. An inspection area is set on the image and a direction is extracted on the image in which a change appears in the color phase according to the arrangement of the light sources and this extracted direction is compared with a preliminarily registered standard direction to judge the surface condition from the result of this comparison.

8 Claims, 11 Drawing Sheets

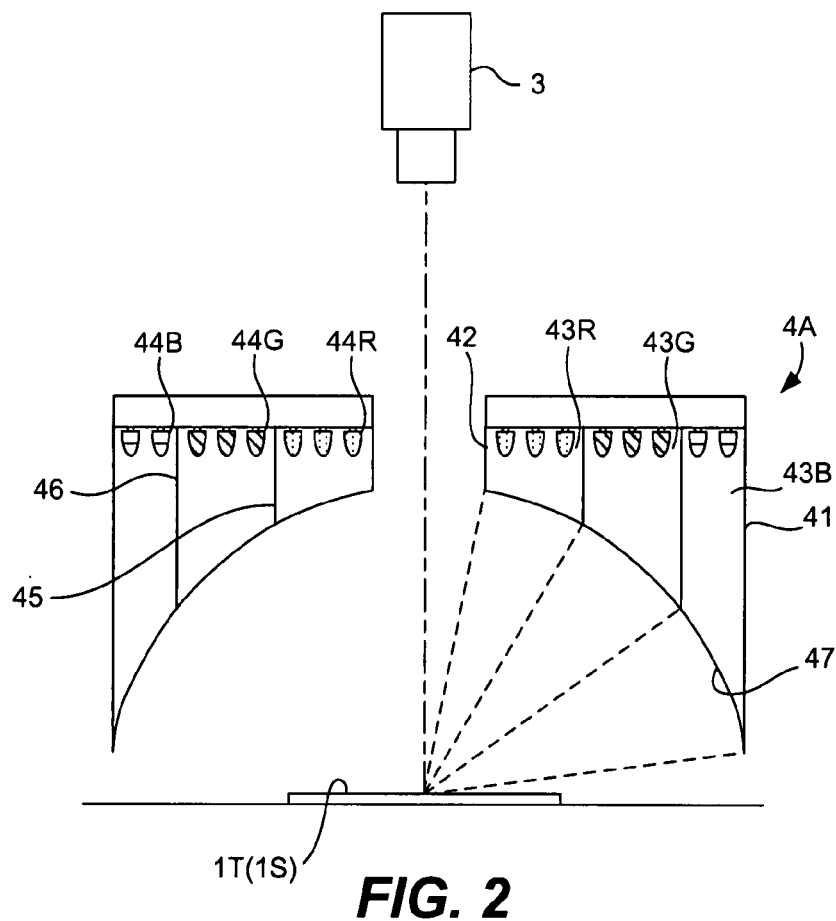
FIG. 2
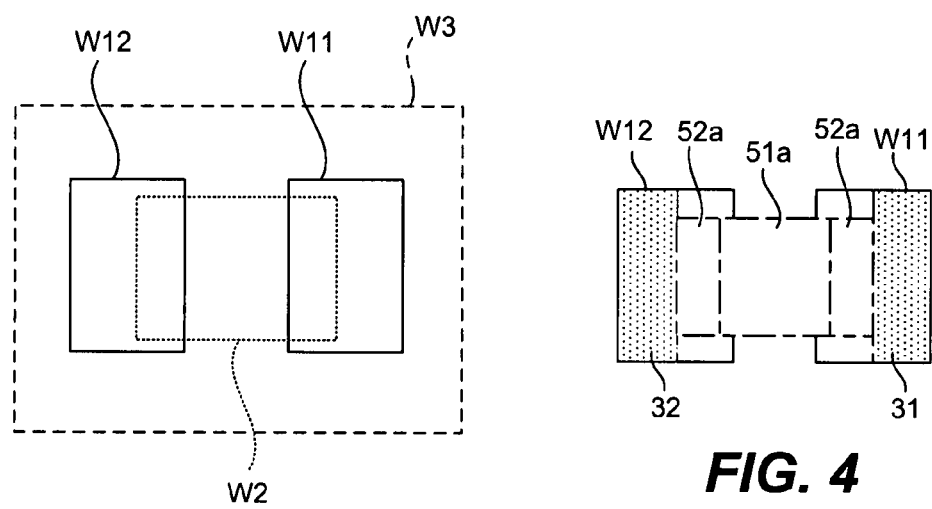
FIG. 3
FIG. 4

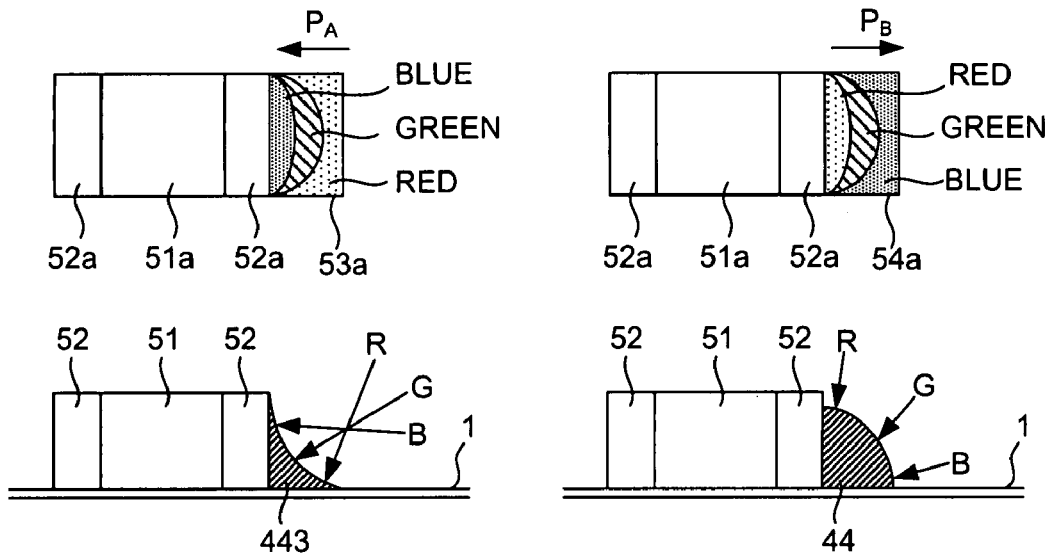
FIG. 5A  FIG. 5B
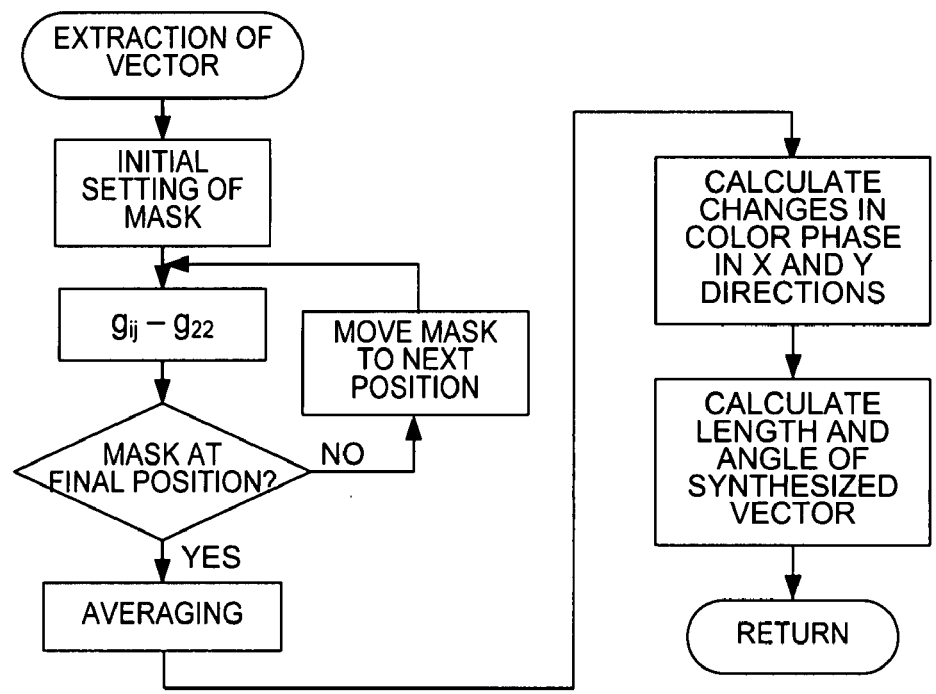
FIG. 6

DATA BY SCAN ON COLUMN 2

| 3 | 3 | 1 |
|---|---|---|
| 6 | 4 | 2 |
| 8 | 5 | 2 |

| 6 | 4 | 2 |
|---|---|---|
| 8 | 5 | 2 |
| 9 | 6 | 4 |

| 8 | 5 | 2 |
|---|---|---|
| 9 | 6 | 4 |
| 8 | 5 | 3 |

| 9 | 6 | 4 |
|---|---|---|
| 8 | 5 | 3 |
| 7 | 3 | 1 |

| 8 | 5 | 3 |
|---|---|---|
| 7 | 3 | 1 |
| 5 | 2 | 1 |

CHANGE IN COLOR PHASE

| -1 | -1 | -3 |
|----|----|----|
| +2 | 0  | -2 |
| +4 | +1 | -2 |

| +1 | -1 | -3 |
|----|----|----|
| +3 | 0  | -3 |
| +4 | +1 | -1 |

| +2 | -1 | -4 |
|----|----|----|
| +3 | 0  | -2 |
| +2 | -1 | -3 |

| +4 | +1 | -1 |
|----|----|----|
| +3 | 0  | -2 |
| +2 | -2 | -4 |

| +5 | +2 | 0  |
|----|----|----|
| +4 | 0  | -2 |
| +2 | -1 | -2 |

FIG. 11

FIG. 12

APPARATUS FOR SURFACE INSPECTION AND METHOD AND APPARATUS FOR INSPECTING SUBSTRATE

Priority is claimed on Japanese Patent Applications P2004-052800 filed Feb. 27, 2004 and P2005-032845 filed Feb. 9, 2005.

BACKGROUND OF THE INVENTION

This invention relates to a method of inspecting the surface condition of an object having a sloped surface with a high specular characteristic by using an image taken thereof, as well as to an apparatus using such a method and particularly to an apparatus for inspecting the surface conditions of a substrate having a plurality of soldered portions.

As disclosed in Japanese Patent Publication Tokko 6-1173, the present applicant has earlier developed an apparatus for automatically inspecting soldered portions of a substrate by an image processing method which makes use of the mirror reflection characteristic of the soldered portions. FIG. 16 shows the structure of such a substrate inspection apparatus and the principle of inspection thereby as disclosed in aforementioned Patent Publication, having three light sources 8, 9 and 10 for emitting red, green and blue light beams, respectively, and an image taking device 3 for obtaining an image of the object of inspection. In the figure, numeral 1 indicates a substrate and numeral 2 indicates a solder piece to be inspected, above which the light sources 8, 9 and 10 are arranged at different angles of elevation with respect to the substrate 1 and the solder piece 2 while the image taking device 3 is set such that the image of the solder piece 2 will be taken directly from above.

With an inspection apparatus thus structured, the colored beams of light from these individual light sources 8, 9 and 10 are projected onto the surface of the solder piece 2 from mutually different directions. If a beam of light is projected onto the sloped surface of solder piece 2 from such a direction that is symmetric with the direction to the image taking device 3 with respect to the line perpendicular to the slope at the point where the light is projected, the mirror-reflection of this projected beam will be directed toward the image taking device 3. In other words, the color of the mirror-reflected light made incident into the image taking device 3 will be different, depending upon the slope of the solder surface.

By the example of optical system shown in FIG. 16, the elevation angle as seen from the solder piece 2 is the largest for the, red light source 8 and that for the blue light source 10 is the smallest, the green light source 9 being positioned in between. Thus, if the solder piece 2 is spherical, as shown in FIG. 17, a color-partitioned image is obtained with the flat surface portion at the center appearing as a red image area, the steeply sloped surface portions close to the substrate surface appearing as a blue image area, and the intermediate gently sloped surface portions appearing as a green image area.

When a fillet of solder is inspected, as shown in FIG. 18, a color-partitioned image is obtained with the steeply sloped upper portion appearing as a blue image area, the gently sloped intermediate portion appearing as a green image area and the nearly horizontal lower portion near the substrate surface appearing as a red image area. In FIG. 18, symbol S1 indicates the range for a land.

In summary, an image partitioned into red, green and blue areas is obtained from a solder piece, depending on the change in the slope of its surface. Thus, the quality of the solder surface condition can be determined if a color image pattern of an ideally shaped solder piece is preliminarily registered and a comparison is made with such a registered pattern.

According to a prior art technology of apparatus for inspection based on the principle as described above, each of the red, green and blue color areas is extracted by preliminarily defining a binarization threshold value for each of red, green and blue gradation data comprising a digital color image and binarizing the image obtained from the image taking device 3 by using these binarization threshold values. Data such as position, shape and size of extracted areas from an image of an ideally shaped solder piece may be preliminarily registered such that the quality of a solder surface may be determined by comparing the colored areas of its image with the registered data.

With the optical system shown in FIG. 16, however, the brightness and the color on the image may be thought to vary as the brightness and the color of the illuminating light changes according to temperature and the time of use, and such variations in the brightness and the color may be considered to affect the result of extraction of the color areas. In the inspection of a solder piece, in particular, if the characteristic quantity of each color area changes due to a change in the color, it may become impossible to clear the standard set for a "good" product although the surface condition may be normal, and such a product may be judged defective.

In order to keep the accuracy of inspection at a high level, therefore, it is desirable to frequently change these binarization threshold values. Since inspection apparatus of this kind are required to keep repeating inspection processes with substrates being supplied incessantly one after another, the work efficiency is severely affected if the inspection must be stopped as the binarization threshold values are updated. Another problem is that it is difficult to judge the correct timing for updating the binarization threshold values.

As an alternative to the aforementioned binarization process, a pattern matching process may be carried out by using the image of an ideally mounted substrate as a model image. According to this method, since normalized correlation calculations are carried out between the image to be inspected and the model image, the threshold values for the judgment need not be changed although there may be a change in illumination. On the other hand, the correlation value drops even by a small change in the shape of the solder piece being inspected and the probability of obtaining a correct judgment result also deteriorates.

Moreover, the modern tendency is that substrates become smaller and more parts are mounted to them. As a result, the land area corresponding to each component part must be adjusted according to the density of mounting in the surrounding areas. As a result, the land size changes even for a same component, depending on the number of components mounted in the surrounding areas. Since the slope of a solder fillet comes to vary accordingly, depending on the mounting position of the component and hence the size and shape of each color area of a fillet image also become different. If there are relatively few components mounted near by, for example, the land may be made relatively big for the soldering stability and hence the slope of the fillet becomes gentler and the red, green and blue areas appear properly. In the case of a component mounted where the mounting density is relatively large, on the other hand, the land area must be accordingly diminished and the slope of the fillet becomes steep, the blue area becoming dominant and the green and red areas becoming smaller. Thus, the distribution of color areas on the image changes even for components of the same kind and hence the standard of judgment for each color area must be set for each component in order to maintain a high level of inspection accuracy.

SUMMARY OF THE INVENTION

The present invention was accomplished in view of the problem described above and its primary object is to make it possible to inspect a sloped surface even if there are changes in the brightness and color of the image.

Another object of this invention is to make it possible to accurately inspect even a surface with steep or gentle slopes such that color areas corresponding to all of the light sources may not be easily produced.

According to a method of this invention for inspecting the surface condition of a target object having slopes on its surface, a plurality of light sources for emitting light of different colors are set, each arranged so as to have a different elevation angle with respect to the target object at an inspection position and light is projected from these light sources. An image of the target object taken by a camera unit positioned above the inspection position of the target object is used for the inspection. The method of inspection comprises the steps of setting an inspection area including the target object on the image, extracting in the inspection area a direction in which a change in color phase appears corresponding to arrangement of each of the light sources, making a comparison between the extracted direction and a preliminarily registered standard direction, and judging the surface condition from the result of this comparison.

If the target object is irradiated by thus setting such light sources, colors appear on the portions of the image taken by the camera unit corresponding to a sloped surface according to the angle of the slope. If the slope of the surface changes gradually, the color of the corresponding portion of the image changes in an order corresponding to the order in which the light sources are arranged, that is, the order of their elevation angles.

In the above, "change in color phase corresponding to arrangement of each of the light sources" means the order in which the colors emitted from these light sources will appear as seen from the target object. In the case of an optical system arranged as shown in FIG. 16, this may be understood as the change from red to green to blue or from blue to green to red.

Since colors appear in the order of the arrangement of the light sources, the direction in which colors appear in this order may be regarded as corresponding to the direction in which the slope of the light-reflecting surface is changing. Although the brightness and color phase on the image may change, the direction of change in color phase on the image according to the arrangement of the light sources is believed not to change. Thus, if a model image obtained from a model target object is preliminarily used to determine standard directions where a change in color according to the arrangement of the light sources is expected to appear, directions extracted from an image of a target object being inspected may be compared with these standard directions to determine whether the target object has a correct surface shape.

In the case of many target objects of the same kind among which there are fluctuations in the magnitude of slope, however, it may be believed that the direction of the slope does not change. Thus, if a standard direction is set for one of them, the same standard direction may be used for the other target objects for improving the efficiency of inspection.

According to a preferred embodiment of the invention, the light sources are arranged with respect to the target object such that their colors are aligned in the direction of change of their color phase on the hue circle. If the colors of the light sources are red, green and blue, for example, these light sources are arranged such that their elevation angles will increase in the order of red-green-blue of blue-green-red. A direction is extracted by obtaining for each of pixels in the inspection area one-dimensional color phase data with values changing along the hue circle and extracting the direction such that the color phase data change to larger values or smaller values along the direction.

According to this embodiment, since the light sources are arranged in the order in the direction in which the color phase changes on the hue circle, the corresponding change in the color phase on the image also corresponds to the change in the hue circle. Since one-dimensional color phase data with values changing along the hue circle are used, the direction in which the color phase is changing corresponding to the arrangement of the light sources can be represented as the direction in which the color phase increases or decreases. Thus, the direction in which the change appears in the color phase may be easily extracted as the vector based on the change in the color phase.

According to another embodiment of the invention, the direction is extracted by obtaining for each of pixels in the inspection area one-dimensional color phase data that reflect strength of a color component corresponding to any one of the different colors of the light sources and extracting the direction such that the color phase data change to larger values or smaller values along the direction.

If the optical system shown in FIG. 16 is used and the blue component corresponding to the light source 10 of blue light is considered, for example, gradation data B may be considered to increase as the slope becomes steeper and smaller as the slope becomes gentler. Thus, if its magnitude with respect to other color components such as ratio B/R or B/(R+G) or its ratio with respect to brightness B/(R+G+B) may be obtained and used as color phase data. In this case, too, the direction in which a change in the color phase corresponding to the arrangement of the light sources appears may be represented as the direction in which the color phase data becomes larger or smaller. Thus, the direction in which the color phase is changing may be easily extracted as the direction of the vector based on the change in the color phase.

If one-dimensional color phase data are obtained for each pixel and their change is extracted as done in both of the embodiments described above, the direction in which the aforementioned change in the color phase along the hue circle appears may be extracted by extracting changes in the color phase data for each of directions passing through a plurality of selected pixels in the inspection area, setting a plurality of vectors by averaging the extracted changes for each of the directions and obtaining a synthesized vector out of these plurality of vectors. The synthesized vector may be required to be of a sufficient length. If only a vector shorter than a threshold length can be obtained, it may be concluded that there is no sloped surface of a good quality.

An apparatus according to this invention for inspecting surface condition may be characterized as comprising a light-emitting part having a plurality of light sources each for emitting light of a different color and each arranged so as to have a different elevation angle with respect to a target object at an inspection position, a camera unit disposed above the inspection position of the target object, an image input unit that inputs an image created by the camera unit under a condition where each of these light sources is lit, extracting means for setting an inspection area including the target object on the image and extracting in the inspection area a direction in which a change in color phase appears corresponding to arrangement of each of the light sources, registering means for registering a standard direction extracted by the extracting means from a good target object with a good surface condition, judging means for judging surface condition of the target object by comparing the direction extracted by the extracting means from the target object, and outputting means for outputting the result of judgment by the judging means.

In the above, the light-emitting part may include three concentrically disposed ring-shaped light sources each adapted to emit light of a different color and having a different diameter. A plurality of light emitting elements such as LEDs for emitting light of a same color may be arranged in a circular manner as a single light source. The light source need not necessarily be ring-shaped. A linear light source may be used for the purpose of this invention. The camera unit may comprise a CCD camera adapted to create an image signal for each color. If the light-emitting part is formed with ring-shaped light sources, it is preferable to set the camera unit so as to have its optical axis aligned vertically along the center axis of the light sources. The image input unit, the extracting means, the registering means, the judging means and the outputting means may all be set within a same housing structure. The extracting means, the registering means and the judging means may be realized as a computer having programs installed for carrying out the processes by these means. A computer may be provided separately for each of these means or a single computer may be provided for all these means.

The image input unit may be comprised of an amplifier circuit for amplifying the image signal from the camera unit and an A/D converter circuit for converting this image signal into a digital signal. If a digital camera is used in the camera unit, however, the image input unit may be formed as an input port for taking in digital color image data. The extracting means and the judging means are for carrying out the aforementioned extracting, comparing and judging steps. The registering means serves to register in the memory of a computer the standard direction extracted from a model image of a good target object created by the light projecting unit and the camera unit. As for the registering means, it may be defined as the means for having image data processed by the extracting means when an inspection area is set on a model image and storing the extracted direction as the standard direction in the memory. Alternatively, it may be defined as the means for having a direction specified in which the colors of the light sources are arranged on a model image in the order corresponding to the arrangement of the light sources and storing this direction in the memory as the standard direction. The outputting means may comprise a display interface for displaying the judgment result by the judging means or an output interface for outputting the judgment result to an external apparatus. Alternatively, the outputting means may be formed as recording means for recording on a memory medium such as a flexible disk, a CD-R or a photomagnetic disk.

According to a preferred embodiment of the invention, the light sources are arranged such that the different colors are arranged in the direction of change of color phase on the hue circle and the extracting means is set so as to obtain for each of pixels in the inspection area one-dimensional color phase data with values changing along the hue circle and to extract the direction such that the color phase data change to larger values or smaller values along the direction. The light projecting unit is preferably comprised of three light sources for emitting red, green and blue light, respectively, arranged such that their elevation angles will increase in the order of red-green-blue or blue-green-red.

According to another preferred embodiment of the invention, the extracting means is set so as to obtain for each of pixels in the inspection area one-dimensional color phase data that reflect strength of a color component corresponding to any one of the different colors of the light sources and to extract the direction such that the color phase data change to larger values or smaller values along the direction. In this embodiment, too, it is preferable that the light projecting unit be comprised of three light sources for emitting red, green and blue light, respectively, arranged such that their elevation angles will increase in the order of red-green-blue or blue-green-red. If the light projection unit is thus structured, it is preferable to use gradation data R or B as the color component to be used for the color phase data. If B is the selected gradation data, for example, the aforementioned color phase data may be obtained as ratio with respect to another color or the other colors B/R or B/(R+G) or as its ratio with respect to brightness B/(R+G+B). The extracting means may include means for extracting changes in the color phase data for each of directions passing through a plurality of selected pixels in the inspection area, setting a plurality of vectors by averaging the extracted changes for each of the directions and obtaining a synthesized vector out of these vectors.

This invention may be applied to an apparatus for inspecting a substrate having a plurality of components soldered thereonto. Such an apparatus according to this invention may be characterized as comprising a light-emitting part having a plurality of light sources each for emitting light of a different color and each arranged to have a different elevation angle with respect to the substrate, a camera unit disposed above the substrate, an image input unit that inputs an image created by the camera unit under a condition where each of the light sources is lit, extracting means for setting an inspection area including each of soldered portions on the image and extracting in the inspection area a direction in which a change in color phase appears corresponding to arrangement of each of the light sources, registering means for registering a standard direction extracted by the extracting means under a good solder surface condition, judging means for judging condition of each of the soldered portions by comparing the direction extracted by the extracting means from the target object, and outputting means for outputting the result of judgment by the judging means. The extracting means, the registering means, the judging means and the output means of such an apparatus for inspecting a substrate may be structured basically similar to those of the surface inspection apparatus described above.

If components of a same kind are soldered to the target substrate to be inspected, the registering means may be adapted to apply the standard direction obtained for one of the components in the inspection of the others of the components. This function makes it unnecessary to repeat the registration step for each of the components and hence the inspection efficiency can be improved.

As for the standard direction to be registered, it may be set in response to the user's operation or by extracting a direction after the extraction means processes the image of a model target substrate known to be good. When a standard direction is applied to another component of the same kind, if direction of this component is different from that of an earlier registered component, the process of correcting the standard direction by using the difference becomes necessary.

With an apparatus embodying this invention, sloped conditions of soldered positions can be accurately inspected by checking whether the change in the sloped surface of a soldered position is correctly oriented or not. It is also possible to determine whether a sloped solder surface has been formed or not by examining the magnitude of change in the color phase corresponding to the arrangement of the light sources and the positions of change in the color phase. When a plurality of components of a same kind are mounted on a single substrate, furthermore, an inspection can be carried out easily since the standard direction does not vary although the slope of solder may change, depending on how densely components are mounted.

BRIEF DESCRIPTION OF THE DRAWINGS

FIG. 2 is a sectional view of another light projecting part.

FIG. 3 is a drawing for explaining an example of windows being set.

FIG. 4 shows an example of setting an inspection area for the inspection of a fillet.

FIGS. 5A and 5B, together referred to as FIG. 5, show color distribution on an image in an inspection of a fillet and its correlated side view.

FIG. 6 is a flowchart of a routine for extracting a color change vector.

FIG. 11 shows the results of the process of Step ST102 shown in FIG. 6 carried on the color phase data extracted by the scan along the second column.

FIG. 12 shows the results of the process of Step ST102 shown in FIG. 6 carried on the color phase data extracted by the scan along the third column.

DETAILED DESCRIPTION OF THE INVENTION

Figure 1:
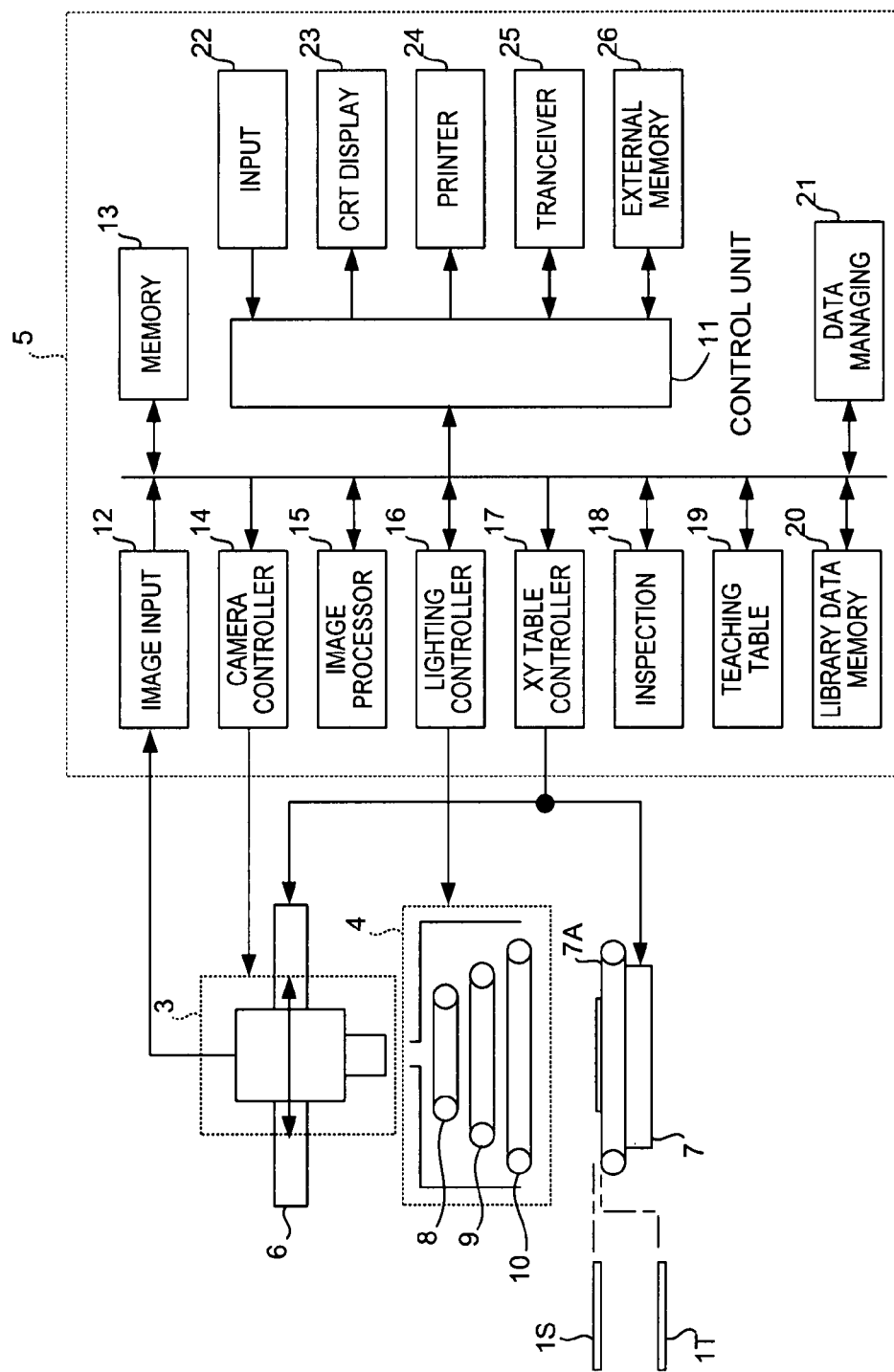
FIG. 1 is a block diagram of a substrate inspection apparatus to which the present invention is applied.

FIG. 1 shows the structure of a substrate inspection apparatus embodying this invention, being adapted to process an image taken of a target substrate to be inspected and to thereby judge whether or not soldering positions and the mounting of components thereon are proper, and comprising an image taking unit (or a camera unit) 3, a light projecting part 4, a control processing part 5, an X-axis table part 6 and a Y-axis table part 7. The target substrate to be inspected is indicated by symbol 1T. Symbol 1S indicates a standard substrate with soldering parts properly formed and components properly mounted, to be used prior to an inspection process for the purpose of "teaching".

The Y-axis table part 7 is provided with a conveyor 7A for supporting the substrates 1S and 1T, serving to move them in the Y-direction (perpendicular to the plane of the figure) by means of a motor (not shown). The X-axis table part 6 serves to support the camera unit 3 and the light projecting part 4 and move them in the X-direction (to the left and right in the figure) above the Y-axis table part 7.

The light projecting part 4 includes three ring-shaped light sources 8, 9 and 10 with different diameters, respectively adapted to emit red light, green light and blue light. Their centers are directly above the observation position such that each of them has a different elevation angle as seen from the substrate 1S or 1T.

The camera unit 3 is a CCD camera for producing a color image with its optical axis oriented vertically and passing through the centers of the three light sources 8, 9 and 10 such that the reflected light from the substrate 1S or 1T will be made incidence to the camera unit 3 and converted into three color signals R, G and B corresponding to the three primary colors to be inputted to the control processing part 5.

The control processing part 5 has a computer with a CPU as its control unit 11 and also includes an image input unit 12, a memory 13, an image taking controller (or a camera controller) 14, an image processor 15, a lighting controller 16, an XY table controller 17, an inspection unit 18, a teaching table 19, a library data memory 20, a data managing unit 21, an input unit 22, a CRT display unit 23, a printer 24, a transceiver unit 25 and an external memory 26.

The image input unit 12 is provided with an amplifier circuit for amplifying each of image signals of the three primary colors from the camera unit 3 and an A/D conversion circuit for converting these image signals into digital signals. The memory 13 serves to store not only digital gradation data for the three colors (hereinafter referred to as gradation data R, G and B) but also binary image data and color phase data which are obtained by processing these gradation data R, G and B.

The camera controller 14 is provided with an interface for connecting the camera unit 3 to the control unit 11 and serves to drive the camera unit 3 according to a command from the control unit 11 and to adjust the output level of each of the color light beams. The lighting controller 16 is for adjusting the quantity of light from each of the light sources of the light projecting part 4. According to the present example, the quantity of light of each of the three light sources 8, 9 and 10 is adjusted such that light of white color is produced for illumination.

The XY table controller 17 includes an interface for connecting the X-axis table part 6 and the Y-axis table part 7 to the control unit 11 and serves to control the motions of the X-axis table part 6 and the Y-axis table part 7 according to commands from the control unit 11.

The teaching table 19 is a memory device for storing inspection data of the substrate. These inspection data include not only the conditions for setting the inspection windows (to be explained below) but also binary threshold values (not only binary threshold values corresponding to R, G and B but also those related to brightness) for extracting the color of each target object such as components, land and solder and judgment standard values (to be set individually for each kind of characteristic quantity such as position and size) for judging characteristic quantities of patterns extracted by these binary threshold values to be good or bad. According to the present example, standard data for color change vector (to be explained below) are also registered as inspection data for a solder fillet.

The library data memory 20 is a memory device for registering standard inspection data for each kind of component (hereinafter referred to as the library data). According to the present example, set data regarding the inspection windows (to be explained below) and the kind of inspection program to be carried out by each inspection window are registered as the library data.

Various kinds of these inspection data to be registered in the teaching table 19 are shown prior to the inspection by using the image obtained by photographing the standard substrate 1S or by using the aforementioned library data and they are summarized as a judgment file for each kind of substrate. The data managing unit 21 is a memory device for storing link data that correlate between the kinds of substrate and the judgment files. After the input of the name of the target substrate 1T for inspection is received, the control unit 11 reads out the judgment file corresponding to this target substrate 1T and sets it to the memory 13 on the basis of the link data of the data managing unit 21. The image processor 15 and the inspection unit 18 carry out processes on the basis of the inspection data in the judgment file which has been read out.

At the time of inspection, the image processor 15 serves to process each of the gradation data R, G and B stored in the memory 13 and to extract parameters of various kinds for judging good and bad. The inspection unit 18 serves to compare the extracted parameters with corresponding inspection data and to thereby determine absence and erroneous positioning as well as the quality of soldering, etc. for each of the mounted components. The control unit 11 gathers the results of these judgments and concludes whether the target substrate 1T is good or bad. This final judgment result is outputted to the CRT display unit 23, the printer 25 or the transceiver unit 25.

The input unit 22 is for inputting the various conditions for inspection and inspection data and is provided with a keyboard and a mouse. The CRT display unit 23 (hereinafter referred to simply as the display unit 23) is adapted to receive image data and inspection results from the control unit 11 and to display them on its display screen. The printer 25 is for receiving image data and inspection results from the control unit 11 and printing them out in a predetermined format.

The transceiver unit 25 is for exchanging data with other apparatus. For example, the identification of a target substrate judged to be bad as well as the reason for such a judgment may be transmitted to a repair apparatus on a later stage such that the defect can be quickly repaired. The external memory 26 is a device for writing data in a memory medium such as a flexible disk, a CD-R or a photomagnetic disk and is used for saving the inspection results and taking in from outside programs and set data necessary for inspection.

Of the above, the image processor 15 and the inspection unit 18 may be formed by a dedicated processor having programs installed for carrying out the described processes but it is not a requirement. Alternatively, the control unit 11 may be provided with the functions of the image processor 15 and the inspection unit 18.

Although the light projecting part 4 was described above as comprising these ring-shaped light sources 8, 9 and 10, FIG. 2 shows another light projecting part 4A which may be used for the purpose of this invention, comprising a housing structure 41 having a cylindrical opening 42 at the center and its interior partitioned into three radially arranged cylindrical chambers 43R, 43G and 43B in the radial direction by means of two cylindrical partition walls 45 and 46. The innermost chamber 43R contains red LEDs 44R, the middle chamber 43G contains green LEDs 44G and the outermost chamber 43B contains blue LEDs 44B each in a plurality of rows. The camera unit 3 is set above the opening 42 at the center such that its optical axis is oriented vertically. The red light, the green light and the blue light that are generated respectively inside the chambers 43R, 43G and 43B are passed through a diffusing plate 47 onto the substrate 1T or 1S. Thus, as by the light projecting part 4 shown in FIG. 1, light of different colors can be projected on the substrate 1T or 1S in different directions at different elevation angles.

Next, an inspection process carried out by the apparatus described above is explained in detail. Although the explanation is given for an example where chip components are mounted to a substrate, it goes without saying that this is not intended to limit the scope of the invention and that components other than chips can be inspected by a similar method.

FIG. 3 shows an example of windows set for the inspection of chip components, including land windows W11 and W12 which are for the inspection of solder and set so as to include the land on the substrate, a component window W2 for inspecting the absence and positional displacement of the component and a standard window W3 which includes the land windows W11 and W12 and the component window W2. The data which define the conditions for setting these inspection windows W11, W12, W2 and W3 (such as their sizes and positions for setting) are automatically created by the processing of the control unit 11 for linking the design data of the substrate (CAD data) and the aforementioned library data. The CAD data include the mounting positions of the components as well as their identification data (such as their component names and type numbers) and the library data are in the form of correlating the identification data such as component names with various kinds of inspection data. The control unit 11 applies the library data on the mounted components to the mounting positions of the components shown by the CAD data on the basis of the aforementioned identification data, thereby determining the sizes of and the positions for setting the inspection windows W11, W12, W2 and W3. The sizes and positions of the windows W11, W12 and W2 thus determined are registered in the teaching table 19 as the aforementioned setting conditions.

At the time of an inspection, each of the inspection windows W11, W12, W2 and W3 is set according to the aforementioned registered setting conditions and a land is extracted by means of the standard window W3. Fine adjustments of the setting positions of the land windows W11 and W12 and the component window W2 are effected on the basis of this extraction result.

The extraction of the land may be effected by carrying out the binarization process for extracting the color of the land and then projecting this binary image in the directions of the x-axis and the y-axis. It may also be effected by extracting the edges by converting the image in the standard window W3 into a monochromatic image and then extracting the edges corresponding to the land from the result of this extraction.

After the inspection windows W11, W12 and W2 are set, inspections are carried out for each of them based on the registered inspection data. For the component window W2, the aforementioned threshold values for binarization are used in a conventional manner to extract a color pattern of the component and an inspection is carried out by using characteristic quantities related to this color pattern such as its area or center of gravity. Thus, the fillet inspection which is carried out with the land windows W11 and W12 will be explained in detail in what follows.

When a fillet is inspected, the portions of the areas of the image inside the land windows W11 and W12 between the end edges of a component electrode 52a to the outer edges of the land windows W11 and W12 (that is, the dotted portions shown in FIG. 4) become the objects of inspection. In what follows, these portions 31 and 32 will be referred to as the inspection areas 31 and 32. In FIGS. 4 and 5, the image of the main body of a chip component is indicated by symbol 51*a* and the image of each of its electrodes is indicated by symbol 52*a*.

FIGS. 5A and 5B each show a color distribution appearing on the image for the inspection of a solder fillet 53 on a chip component (with component main body 51 and its electrodes 52) and its side view. FIG. 5A shows a situation when the fillet 53 has a good shape, having a steep slope near the component main body 51, a flat portion near the substrate 1 and a gentle slope in between such that the color on the image changes from red to green to blue in the direction $P_A$ from the lower edge of the fillet 53*a* to its upper edge. FIG. 5B shows a bad situation where no fillet is formed because of insufficient affinity or due to an excess of the solder material resulting in a swelling solder body 54 having a flat portion near the component main body 51, a steeply sloped portion near the substrate 1 and a gently sloped portion in between. Thus, the color of the swelling solder body 54 changes oppositely to the situation with a good product, changing from red to green to blue in the direction $P_B$ from the upper edge to the lower edge.

Thus, the distribution of colors on the image changes, depending on the condition of the slope of the solder surface except that the color always changes from red to green to blue from where the slope of the inclined surface is small to where it is large. This change is the same as the change along the hue circle. Accordingly, if one-dimensional color phase data are obtained for each of the pixels in each of the inspection areas 31 and 32 such that data value decreases as the red color becomes stronger and increases as the blue color becomes stronger and if the change in the color phase data is calculated in each direction, the quantity of this change becomes greater than a specified value in the direction such as directions $P_A$ and $P_B$ shown in FIG. 5 in which the color changes from red to green to blue. In directions in which a change in color in this order does not appear, however, the quantity of this change in color phase is smaller than this specified value. In a direction in which the color changes from blue to green to red, furthermore, the quantity of this change in color phase becomes a negative quantity.

Thus, a "color change vector" is defined in the direction in which the color phase changes from red to blue and color change vectors according to this definition are extracted in this example from the aforementioned one-dimensional color phase data. The magnitudes and directions of the color change vectors thus extracted are used to evaluate the quality (whether good or bad) of a fillet.

The image processor 15, referred to above, serves to extract these color change vectors by converting three-dimensional image data for each of the pixels in the inspection areas 31 and 32 each comprising gradation data R, G and B into one-dimensional color phase data H. This conversion process is carried out by mutually comparing the values of R, G and B, determining which of them has a maximum value $V_{max}$ and selecting one of the formulas (1), (2) and (3) given below accordingly:

$$H=(bb-gg)*\pi/3 \text{ if } R=V_{max}, \tag{1}$$

$$H=2+(rr-bb)*\pi/3 \text{ if } G=V_{max}, \text{ and} \tag{2}$$

$$H=4+(gg-rr)*\pi/3 \text{ if } B=V_{max} \tag{3}$$

where $$rr=(V_{max}-R)/(V_{max}-V_{min}), \tag{4}$$

$$gg=(V_{max}-G)/(V_{max}-V_{min}), \text{ and} \tag{5}$$

$$bb=(V_{max}-B)/(V_{max}-V_{min}) \tag{6}$$

where $V_{min}$ is the smallest of R, G and B.

If R, G and B are 8-bit data for 256 gradations, the value of the color phase data H varies theoretically within the range between 0 and $(4+\pi/3)$, H assuming its minimum value of 0 when R=255, G=B=0 and H assuming its maximum value of $(4+\pi/3)$ when R=G=0 and B=255. A correction may be made on H according to (7) as given below:

$$H1=H*10/(4+\pi/3) \tag{7}$$

such that the value of corrected color phase data H1 varies within the numerical range of 0-10. Both H and H1 become smaller as the red becomes stronger and larger as the blue becomes stronger. Thus, if there is a change greater than the aforementioned specified value in the color phase data H1 within the inspection areas 31 and 32, the direction of this change may be defined as the direction of the color change vector.

FIG. 6 is a flowchart of a routine for extracting a color change vector based on the principle described above. FIGS. 7-13 are referenced next as an example to explain this routine in detail. In FIGS. 7-13, the direction from the left to the right is defined as the positive x-direction and the upward direction is defines as the positive y-direction. The target component being inspected is assumed to have its width in the x-direction.

Figure 7:
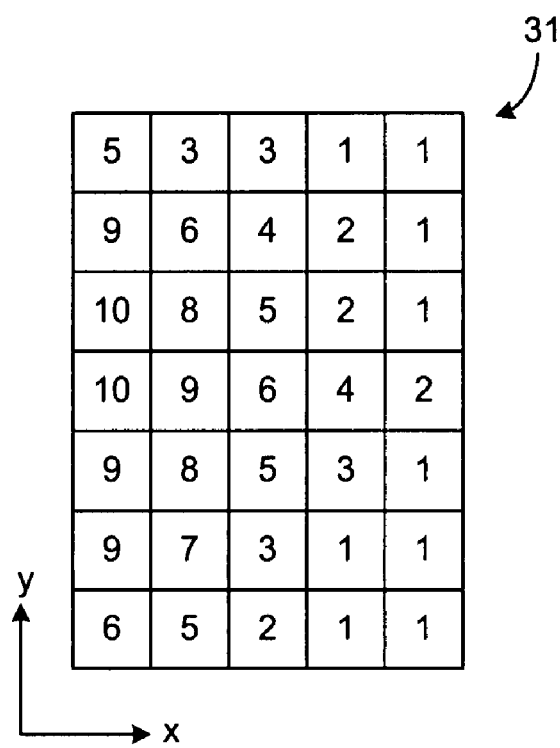
FIG. 7 shows an example of calculated color phase data in an inspection area.

FIG. 7 shows an example of calculated color phase data H1 in the inspection area 31 set inside the right-hand land window W11 for the chip component 21. For simplifying the explanation, it is assumed that the pixels inside this inspection area 31 are arranged in 5 columns and 7 rows.

Figure 8:
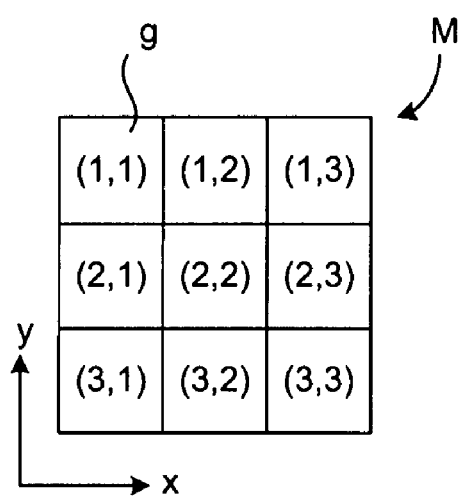
FIG. 8 shows the structure of a mask which scans the inspection area.

According to the routine shown by the flowchart of FIG. 6, a mask M corresponding to 3 pixels by 3 pixels as shown in FIG. 8 is initially set at the left-hand top position of the inspection area (Step ST101). In what follows, the 3×3=9 pixels g within this mask M are indicated by their coordinates (i, j) where i, j=1, 2 and 3 according to their column and row positions.

Next in the routine (Step ST102), differences ($g_{ij}$-$g_{22}$) in color phase are calculated inside the mask M between each of its pixels and the pixel at the center. These differences represent the changes in color phase in all eight directions as seen from the center pixel and their values are stored in the memory 13 in correlation with the coordinates of that pixel in that mask M.

Figure 9:
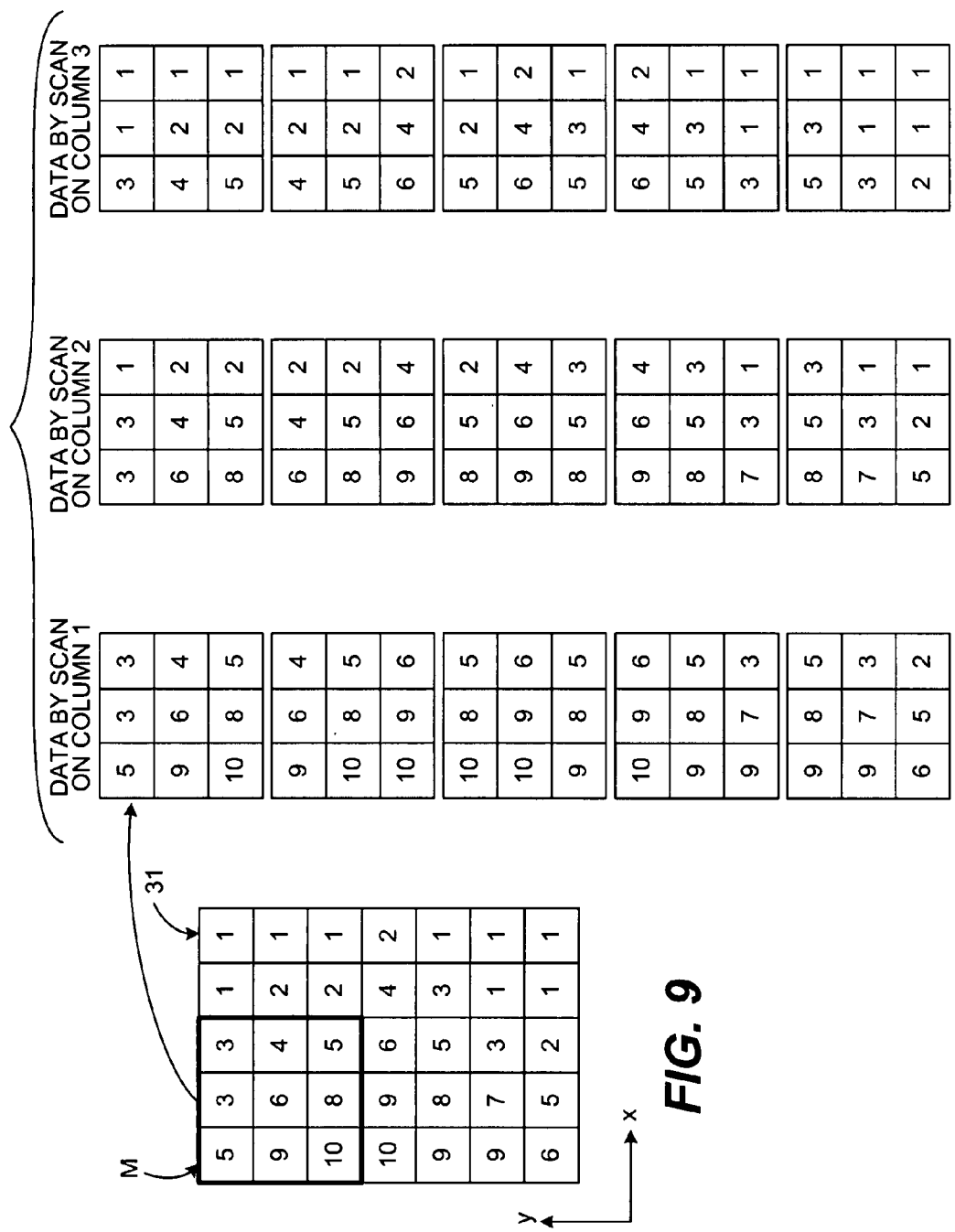
FIG. 9 shows an example of data extracted from the inspection area by the scanning with the mask.

The process in Step ST102 is repeated thereafter by moving the mask M each time to the position of the next pixel until the mask M reaches its final position at the right-hand bottom position of the inspection area (Steps ST102-ST104). FIG. 9 shows the structure of the color phase data extracted from the mask M at each of its positions as it is moved to scan the inspection area 31. For the convenience of description, it will be assumed that the mask M is moved downward firstly along the left-hand edge of the inspection area 31 and it will be referred to as the scan along the first column. Next, the mask M is moved to the right to the position of the next pixel and moved again downward along the y-axis, and this will be referred to as the scan along the second column. Finally, the movement of the mask M along the right-hand edge of the inspection area 31 will be referred to as the scan along the third column.

Figure 10:
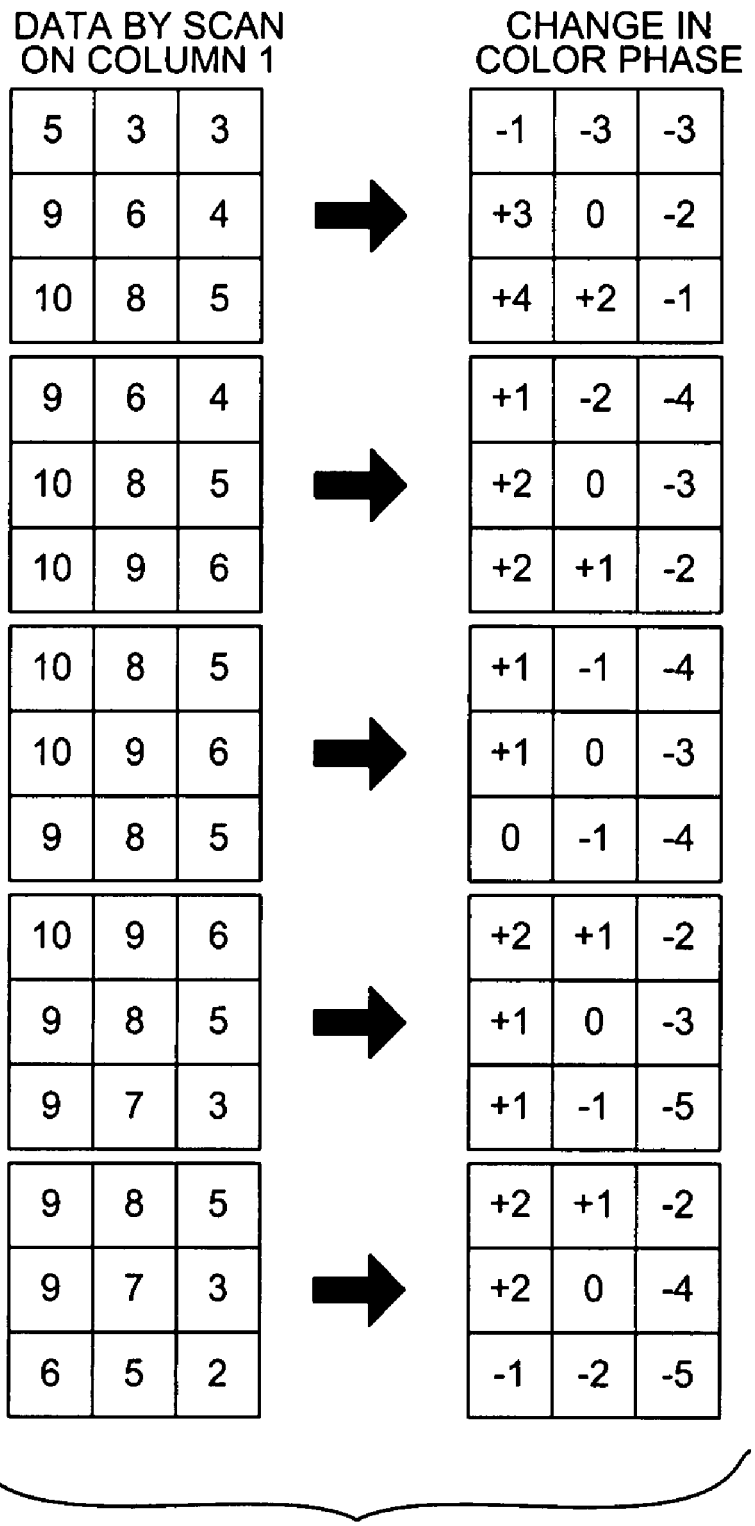
FIG. 10 shows the results of the process of Step ST102 shown in FIG. 6 carried on the color phase data extracted by the scan along the first column.

FIG. 10 shows the results of the process of Step ST102 as it is done to the color phase data extracted by the mask M at each of its positions in its scan along the first column. FIGS. 11 and 12 show similar results obtained from the scan along the second column and the third column, respectively.

Thus, the loop of Steps ST12-ST14 is repeated 3×5=15 times and 15 sets of data arrangement are obtained, each representing the changes in color phase in all eight directions. Thereafter, an averaging process is carried out on these changes in color phase for each of the eight directions (Step ST105). Explained more in detail, average values $I_{ij}$ are calculated from these 15 sets of data arrangement for each set of the sets of pixels at the same coordinates. Regarding the pixels $g_{11}$ at the left-hand top of the mask at each of the scan positions, for example, average value $I_{11}$ is obtained as +1.8 from the change values of $g_{11}$ at all of the scan positions, that is, −1, +1, +1, +2 and +2 from the first column, −1, +1, +2, +4 and +5 from the second column and +1, +2, +1, +3 and +4 from the third column. Average values $I_{12}$-$I_{33}$ are similarly obtained for the other pixels $g_{12}$-$g_{33}$, as shown in FIG. 13.

Figure 13:
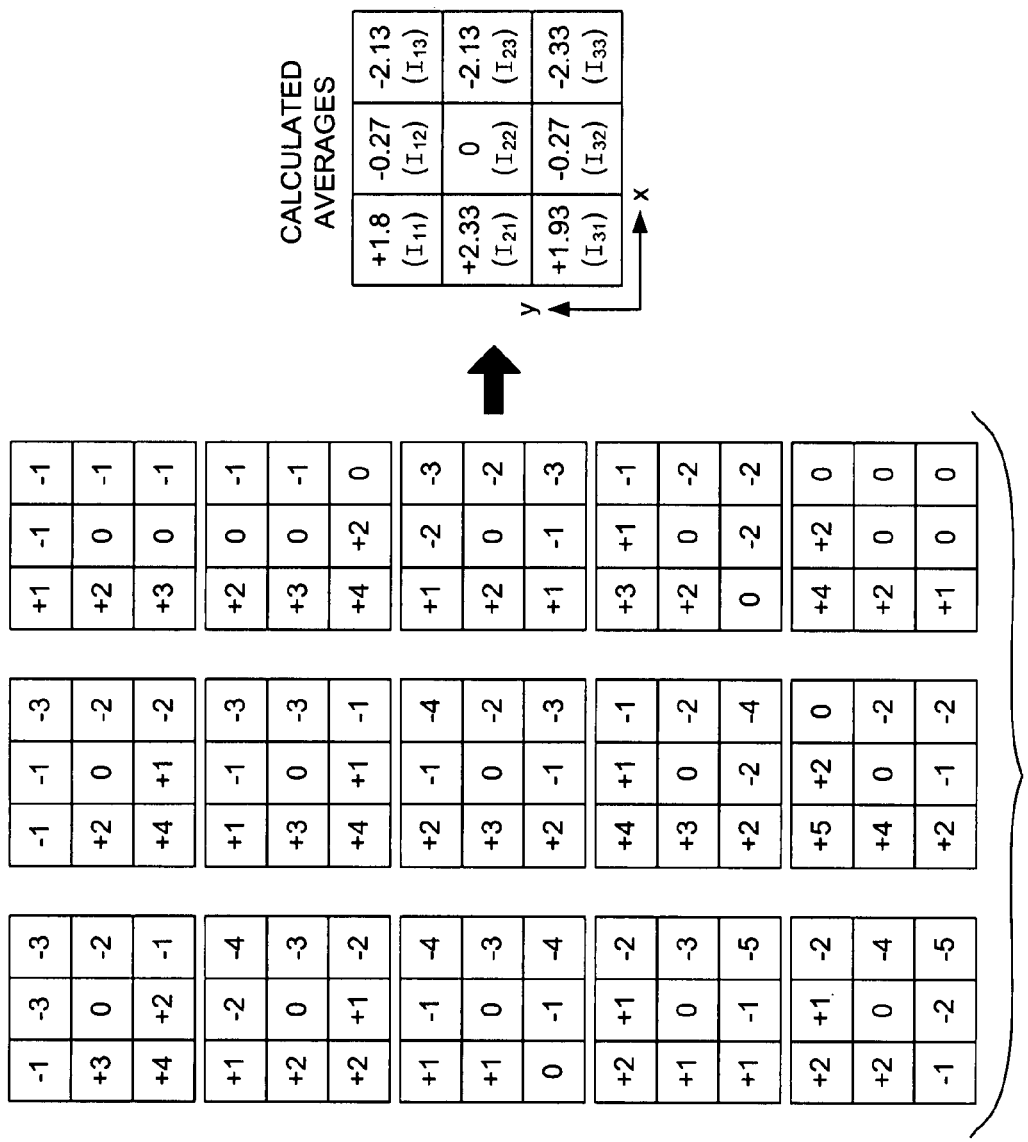
FIG. 13 shows the results of the averaging process of Step ST105 shown in FIG. 6.

According to this example resulting in the average values shown in FIG. 13, it is noted that the average values $I_{11}$, $I_{21}$ and $I_{31}$ corresponding to pixels $g_{11}$, $g_{21}$ and $g_{31}$ on the left-hand side of the center pixel $g_{22}$ are positive and that the average values $I_{13}$, $I_{23}$ and $I_{33}$ corresponding to pixels $g_{11}$, $g_{21}$ and $g_{31}$ on the left-hand side of the center pixel $g_{22}$ are negative. It can thus be concluded at least qualitatively that the color change vector is pointing generally in the direction of the negative x-axis.

In order to determine the direction of the color change vector more accurately, the average values $I_{ij}$ calculated in Step ST105 are used to calculate the changes $C_x$ and $C_y$ in the color phase respectively in the x-direction and the y-direction (Step ST106). This calculation is carried out according to (8) and (9) given below from the principle of the Sobel filter used in the edge extraction process from a gradation image:

$$C_x = (I_{13} + 2I_{23} + I_{33}) - (I_{11} + 2I_{21} + I_{31}), \text{ and} \quad (8)$$

$$C_y = (I_{11} + 2I_{12} + I_{13}) - (I_{31} + 2I_{32} + I_{33}). \quad (9)$$

The changes $C_x$ and $C_y$ thus calculated may be regarded respectively as the x-component and the y-component of the color change vector indicating the direction in which the color phase data increase. In other words, the length (modulus) and the direction of the color change vector can be obtained from $C_x$ and $C_y$ (Step ST107). Explained more in detail, the angle $\theta$ made by the color change vector with the positive direction of the x-axis is defined as follows:

$\theta = \tan^{-1}(C_y/C_x)$ if $C_x > 0$ and $C_y \geq 0$, $\theta = \tan^{-1}(C_y/C_x) + 360$ if $C_x > 0$ and $C_y < 0$, $\theta = \tan^{-1}(C_y/C_x) + 180$ if $C_x < 0$, $\theta = 0$ if $C_x = 0$ and $C_y > 0$, and $\theta = 180$ if $C_x = 0$ and $C_y < 0$.

The length D (modulus) of the color change vector is given by:

$$D = \{C_x^2 + C_y^2\}^{1/2}.$$

In the case of the present example, one obtains $C_x = -17.11$ and $C_y = 0.07$, and this means that the change of the color phase from red to blue can be represented by a vector which points in the negative direction along the x-axis and in the positive direction along the y-axis. The calculations in Step ST107 show that $\theta = 179.77°$ and $D = 17.11$.

Since the data shown in FIG. 7 relates to the inspection area 31 set inside the right-hand land window X11 as shown in FIG. 4, the desirable direction of the color change vector in this area is the one shown by arrow $P_A$ in FIG. 5A, or the negative x-direction. Thus, it may be concluded in the case of the data shown in FIG. 7 that the fillet is in a good condition in the inspection area 31.

According to the present example of procedure for the inspection of a fillet, the direction of the extracted vector is compared with a preliminarily registered standard direction. If the length of the extracted vector is shorter than a preliminarily specified threshold length, however, it is concluded that there is no change in color phase from red to blue within the inspection area. In other words, it is concluded that there is no sloped surface representative of a fillet.

Figure 14:
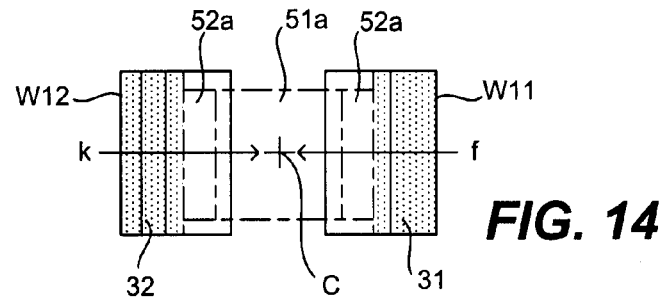
FIG. 14 shows an example of inputted standard direction for the color change vector.
Figure 16:
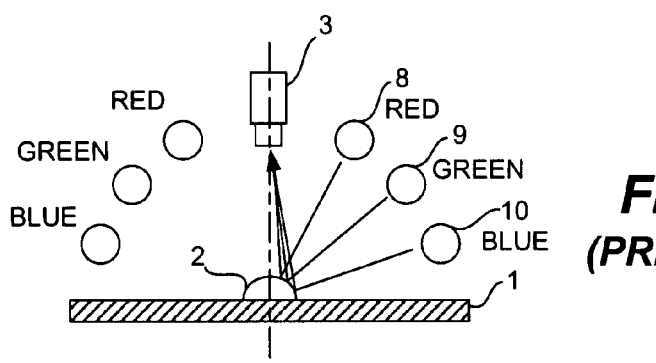
FIG. 16 is a drawing for showing the structure of the optical system of a prior art apparatus for inspecting a substrate.
Figure 17:
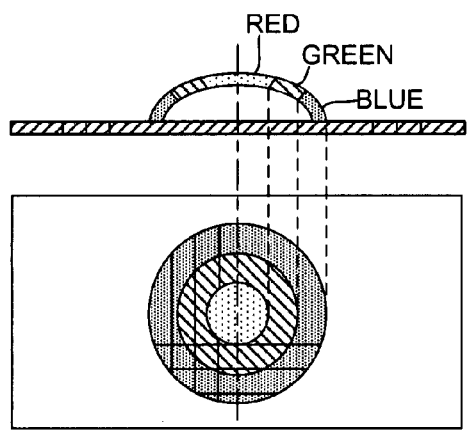
FIGS. 17 and 18 are drawings for showing the principle of recognizing a solder piece by the optical system shown in FIG. 16.
Figure 18:
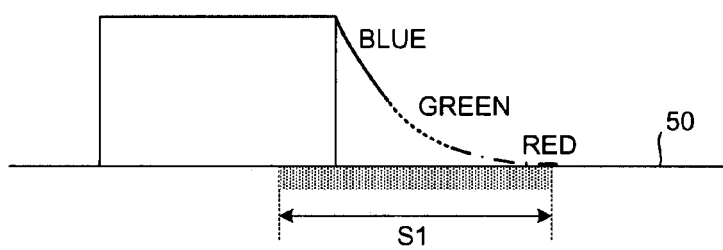

FIG. 14 shows an example of inputted standard direction for the color change vector. According to this example, the user moves a cursor from an edge portion of the land towards the center C of the component while visually observing the direction of the color change from red to green to blue on the image, thereby indicating the standard direction by the motion of the cursor (indicated by arrows f and k in the figure). Each of the indicated directions f and k is converted into an angle made with the positive x-direction and registered in the teaching table 19.

Figure 15:
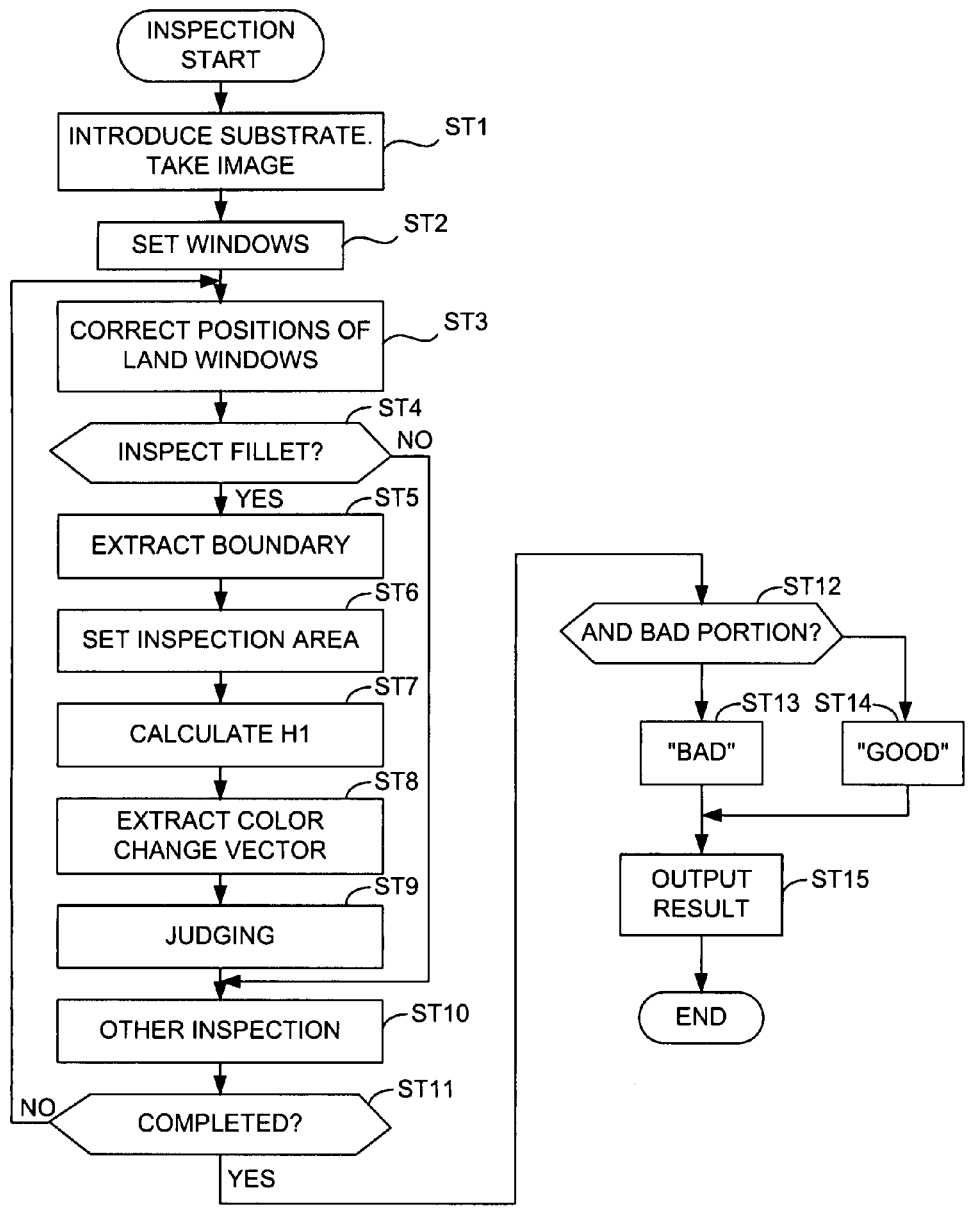
FIG. 15 is a flowchart of the inspection procedure for the apparatus of FIG. 1.

FIG. 15 shows the procedure for inspection by using the apparatus described above for the inspection of a substrate. Prior to the execution of this procedure, however, it is assumed that the operator has already inputted the name of the target substrate 1T through the input unit 22 and the judgment file corresponding to this target substrate 1T has already been read out and set in the memory 13. It is to be understood that the procedure shown in FIG. 15 is only for this target substrate 1T and hence is to be repeated any number of times according to the number of substrates there are to be inspected.

The routine starts as the target substrate 1T is introduced to the Y-axis table part 7 and the image taking step is started by the camera unit 3 (Step ST1). Next, the control unit 11 positions the camera unit 3 and the light projecting part 4 to the target substrate 1T according to the positioning data in the aforementioned judgment file, produces an image of the target substrate 1T and sets the inspection windows W11, W12, W2 and W3 to each of the components on the created image (Step ST2).

Next, lands on both sides of the standard window W3 are extracted regarding a first of the components to be inspected and the positions of the land windows W11 and W12 are adjusted according to the result of this extraction (Step ST3). Next, it is checked regarding this component whether or not an inspection for a fillet should be carried out (Step ST4). If it is decided that this inspection is to be carried out (YES in Step ST4), Steps ST5-ST9 are subsequently carried out sequentially.

Steps ST5-ST9 are carried out individually for both of the land windows W11 and W12. For the convenience of description, however, only the process steps at the land window W11 will be explained. It is also assumed that the component being inspected has its width aligned in the x-direction.

In Step ST5, the boundary position between the electrode and the fillet inside the land window W11 is extracted. For this purpose, binarization threshold values (each for R, G and B) for extracting the color of the image of the electrode (usually reddish) and the numbers of pixels corresponding to the length and the width of the electrode are preliminarily registered in the judgment file, although these data may be transferred from the library data. These binarization threshold values are used to binarize the image inside the land window W11 and a line along which the color of the electrode appears over a length corresponding to the number of pixels representing the length or the width of the electrode is extracted by sequentially observing lines that are perpendicular to the search direction defined from the interior of the land window W11 to the outside. The x-coordinate of the search position where the condition of extracting lines showing the color of the electrode changes is determined as the boundary between the electrode and the fillet.

After the boundary between the electrode and the fillet is thus extracted, the inspection area 31 is set between the position of the extracted boundary and the outer edge of the land window W11 (Step ST6). Next, the color phase data H1 are obtained for each of the pixels in this inspection area 31 by using Formulas (1)-(7) (Step ST7). Thereafter, these color phase data H1 are used for each pixel to extract a color change vector for the inspection area 31 (Step ST8). In this step, the series of processes shown in FIG. 6 is carried out and the length D and the angle θ of the color change vector are calculated.

Next, the color change vector thus extracted is used to determine whether a fillet is formed or not and the quality of its sloped surface (Step ST9). For this purpose, the length D of this vector is compared to a specified threshold value (say, about 10). If the length D is found to be longer than this threshold value, its angle θ is compared with a preliminarily registered standard angle. If the difference between them is found to be less than a specified threshold value (such as 10°), the fillet is judged to be well formed. If this difference is found to be greater than the threshold value, it is judged that the slope condition of the fillet is improper. If the length D of the vector is found to be less than its threshold value, it is concluded that the inspection area 31 does not include any sloped surface corresponding to a fillet.

If the inspection of a fillet is thus concluded, other inspection processes are carried out (Step ST10) such as the presence or absence of a component and its displacement. Since the invention does not relate to such other inspection processes, no description will be presented.

Thereafter, other components in the image are sequentially inspected. Results of inspection on all these components are temporarily stored in the memory 13. When an inspection on one image is completed, the X-axis table part 6 and the Y-axis table part 7 are operated to change the field of vision of the camera unit 3 to take in more images and similar inspection processes are repeated on the components found on the newly obtained image.

When all components have been inspected (YES in Step ST11), it is determined on the basis of the judgment results stored in the memory 13 whether or not there has been any portion which was found to be "bad" (Step ST12). If there was any portion that has been found to be "bad" (YES in Step ST12), this target substrate 1T is judged to be "bad" (Step ST13). If none of its components has been found to be "bad" (NO in Step ST12), the target substrate 1T is determined to be "good" (Step ST14). This judgment result is outputted (Step ST15) and the procedure is completed.

Although the invention has been described by way of an example, this example is not intended to limit the scope of the invention. Many modifications and variations are possible within the scope of the invention. For example, the standard direction of the color change vector need not be registered by the operator's operation at the time of teaching. It may be arranged such that the color change vectors inside the land windows W11 and W12 are extracted and registered by a process similar to that of the inspection. In this manner of operation, the color change vector extracted at the time of inspection can be compared with the registered vector. It may also be arranged such that the position of extraction of the color change vector is also registered at the time of teaching. In this manner, the displacement of a fillet may be detected by comparing the position of extracting the color change vector at the time of inspection with the registered position of extraction.

If many components of a same kind are mounted onto a substrate, the standard direction of the color change vector registered for one of them may be used for the others. Although fillets on components of the same kind may have different slopes, depending on how densely components are mounted in the environment, the direction of the color change vector is invariable. Thus, common inspection data may be usable although there may be fluctuations among the slopes of the fillets on components of the same kind, and this improves the teaching efficiency. Even in the case of a small land that causes the fillet to slope steeply such that only a blue area can be extracted by the binarization process, the direction of change of its slope can be extracted by using a color change vector. Thus, the accuracy of inspection on fillets can be significantly improved according to this invention. It now goes without saying that the standard direction of a color change vector may be stored as library data.

Although the aforementioned color phase data H1 are for indicating the position of the color of a pixel in a hue circle, gradation data B corresponding to a blue light source, for example, may be expressed as color phase data b=100B/(R+B+G), indicative of the ratio of the blue component among the color components that determine the brightness of a pixel, becoming larger where the blue component is strong and smaller where the red component is strong. Thus, a color change vector may be set in a similar manner on the basis of the color phase data b and the direction of the slope of a fillet can be determined from the direction of such a vector.

The three light sources 8, 9 and 10 referenced above may be structured as white light sources such that an image is taken each time they are sequentially switched on. In such an application, the three density-varying image data obtained correspondingly may be treated as R, G and B gradation data and since a color change vector can be extracted, a fillet can be inspected by a similar algorithm.

What is claimed is:

1. A method of inspecting surface condition of a target object having a slope on surface, said method comprising the steps of:

setting a plurality of light sources emitting light of different colors each arranged so as to have a different elevation angle with respect to said target object at an inspection position;

projecting light from said light sources on said target object at said inspection position;

obtaining an image of said target object by a camera unit positioned above said inspection position;

setting an inspection area including said target object on said image;

converting three-dimensional image data comprising gradation data of color components corresponding to said plurality of light sources for each of pixels in said inspection area into one-dimensional color phase data;

observing sequentially a plurality of pixels in said inspection area, based on said color phase data, and calculating differences in color phase data between said observed pixels and neighboring pixels as changes in the color phase data;

defining as standard direction the direction in which specified one of the color components corresponding to said light sources changes to another specified one of the color components corresponding to said light sources along the direction in which the slope on said surface changes when surface conditions of the target object in said inspection area are suitable and preliminarily setting said standard direction;

extracting by using said calculated changes in color phase data a direction along which said color phase data change to larger values indicating higher intensities or smaller values indicating lower intensities, and specifying a direction in which color phase of light corresponding to arrangement of each of said light sources changes on said image along sloped surface of said target object;

making a comparison between said specified direction and the preliminarily set standard direction; and judging appropriateness of said sloped surface of said target object from the result of said comparison and thereby determining appropriateness of the surface condition of said target object.

2. The method of claim 1 wherein said light sources are arranged such that said different colors are arranged in the direction of change of color phase on a hue circle, said direction being extracted by obtaining for each of pixels in said inspection area one-dimensional color phase data with values changing along said hue circle and extracting said direction such that said color phase data change to larger values indicating higher intensities or smaller values indicating lower intensities along said direction.

3. The method of claim 2 wherein said direction is extracted by extracting changes in said color phase data for each of directions passing through a plurality of selected pixels in said inspection area, setting a plurality of vectors by averaging the extracted changes for each of the directions and obtaining a synthesized vector out of said plurality of vectors.

4. An apparatus for inspecting surface condition, said apparatus comprising:

a light-emitting part having a plurality of light sources each for emitting light of a different color and each arranged so as to have a different elevation angle with respect to a target object at an inspection position;

a camera unit disposed above said inspection position of said target object;

an image input unit that inputs an image created by said camera unit under a condition where each of said light sources is lit;

setting means for setting an inspection area including said target object on said image;

converting means for converting three-dimensional image data comprising gradation data of color components corresponding to said plurality of light sources for each of pixels in said inspection area into one-dimensional color phase data; p1 observing sequentially a plurality of pixels in said inspection area, based on said color phase data, and calculating differences in color phase data between said observed pixels and neighboring pixels as changes in the color phase data; extracting means for extracting by using said calculated changes in color phase data a direction along which said color phase data change to larger values indicating high intensities or smaller values indicating lower intensities, and specifying a direction in which color phase of light corresponding to arrangement of each of said light sources changes on said image along sloped surface of said target object;

standard direction setting means for defining as standard direction the direction in which specified one of the color components corresponding to said light sources changes to another specified one of the color components corresponding to said light sources along the direction in which the slope on said surface changes when surface conditions of the target object in said inspection area are suitable and preliminarily setting said standard direction;

comparing means for making a comparison between said extracted direction and said preliminarily set standard direction;

judging means for judging appropriateness of surface condition of said target object by comparing the direction extracted by said extracting means from said target object with said standard direction; and outputting means for outputting the result of judgment by said judging means.

5. The apparatus of claim 4 wherein said light sources are arranged such that said different colors are arranged in the direction of change of color phase on a hue circle, said extracting means obtaining for each of pixels in said inspection area one-dimensional color phase data with values changing along said hue circle and extracting said direction such that said color phase data change to larger values indicating higher intensities or smaller values indicating lower intensities along said direction.

6. The apparatus of claim 5 wherein said extracting means extracts changes in said color phase data for each of directions passing through a plurality of selected pixels in said inspection area, sets a plurality of vectors by averaging the extracted changes for each of the directions and obtains a synthesized vector out of said plurality of vectors.

7. An apparatus for inspecting a substrate having a plurality of components soldered thereonto, said apparatus comprising:

a light-emitting part having a plurality of light sources each for emitting light of a different color and each arranged to have a different elevation angle with respect to the substrate;

a camera unit disposed above the substrate;

an image input unit that inputs an image created by said camera unit under a condition where each of said light sources is lit;

setting means for setting an inspection area including each of soldered portions on said image;

converting means for converting three-dimensional image data comprising gradation data of color components corresponding to said plurality of light sources for each of pixels in said inspection area into one-dimensional color phase data;

observing sequentially a plurality of pixels in said inspection area, based on said color phase data, and calculating differences in color phase data between said observed pixels and neighboring pixels as changes in the color phase data;

extracting means for extracting by using said calculated changes in color phase data a direction along which said color phase data change to larger values indicating high intensities or smaller values indicating lower intensities, and specifying a direction in which color phase of light corresponding to arrangement of each of said light sources changes on said image along sloped surface of said target object;

standard direction setting means for defining as standard direction the direction in which specified one of the color components corresponding to said light sources changes to another specified one of the color components corresponding to said light sources along the direction in which the slope on said surface changes when surface conditions of the target object in said inspection area are suitable and preliminarily setting said standard direction;

comparing means for making a comparison between said extracted direction and said preliminarily set standard direction;

judging means for judging appropriateness of condition of each of the soldered portions by comparing the direction extracted by said extracting means with said standard direction; and outputting means for outputting the result of judgment by said judging means.

8. The apparatus of claim 7 wherein said plurality of soldered components are of a same kind, said apparatus applying the standard direction obtained for one of said components in the inspection of the others of said components.

* * * * *